(12) United States Patent
Sharratt et al.

(10) Patent No.: US 11,897,832 B2
(45) Date of Patent: Feb. 13, 2024

(54) METHOD FOR PREPARING PARTIALLY FLUORINATED ALCOHOL

(71) Applicant: Mexichem Fluor S.A. de C.V., San Luis Potosi (MX)

(72) Inventors: Andrew Sharratt, Runcorn (GB); David Grundy, Runcorn (GB); Ira Saxena, Runcorn (GB)

(73) Assignee: MEXICHEM FLUOR S.A. DE C.V., San Luis Potosi (MX)

( * ) Notice: Subject to any disclaimer, the term of this patent is extended or adjusted under 35 U.S.C. 154(b) by 0 days.

(21) Appl. No.: 17/439,523

(22) PCT Filed: Mar. 18, 2020

(86) PCT No.: PCT/GB2020/050701
§ 371 (c)(1),
(2) Date: Sep. 15, 2021

(87) PCT Pub. No.: WO2020/188274
PCT Pub. Date: Sep. 24, 2020

(65) Prior Publication Data
US 2022/0153668 A1  May 19, 2022

(30) Foreign Application Priority Data
Mar. 21, 2019 (GB) .................... 1903909

(51) Int. Cl.
C07C 29/64 (2006.01)
C07B 39/00 (2006.01)
C07C 29/62 (2006.01)

(52) U.S. Cl.
CPC .............. *C07C 29/64* (2013.01); *C07B 39/00* (2013.01); *C07C 29/62* (2013.01)

(58) Field of Classification Search
CPC .......... C07C 29/62; C07C 29/64; C07C 31/38; C07B 39/00; C07D 303/08; C07D 301/26
See application file for complete search history.

(56) References Cited

U.S. PATENT DOCUMENTS

| 4,798,680 A * | 1/1989 | Nohira ................... C09K 19/06 |
| | | 252/299.5 |
| 5,276,218 A * | 1/1994 | Bohm ..................... C07C 31/38 |
| | | 568/842 |
| 2010/0108934 A1 | 5/2010 | Flynn et al. |

FOREIGN PATENT DOCUMENTS

| JP | H02-167240 A | 6/1990 |
| JP | H02-191233 A | 7/1990 |
| JP | JH02191233 | * 7/1990 ............. C07C 29/64 |

(Continued)

OTHER PUBLICATIONS

Olah, G. A., et al., Synthetic Methods and Reactions, 43. Preparation of Fluorohydrins from Epoxides with Pyridinium Polyhydrogen Fluoride, Israel Journal of Chemistry, vol. 17, pp. 148-149 (Year: 1978).*

(Continued)

*Primary Examiner* — Yate' K Cutliff
(74) *Attorney, Agent, or Firm* — Crowell & Moring LLP

(57) ABSTRACT

A method for preparing a partially fluorinated alcohol, comprises reacting an epoxide: wherein $R^1$, $R^2$, $R^3$ and $R^4$ are independently selected from the group comprising H, F, Cl, Br, I, $CF_3$, alkyl, fluoroalkyl, haloalkyl with a fluorinating agent.

25 Claims, 6 Drawing Sheets

(56) References Cited

FOREIGN PATENT DOCUMENTS

| JP | H02-235828 A | | 9/1990 | |
|---|---|---|---|---|
| JP | H09-110980 A | | 4/1997 | |
| WO | WO 2008/079670 A1 | | 7/2008 | |
| WO | WO2012/098461 | * | 7/2012 | ........... C07D 513/04 |
| WO | WO 2018/165608 A1 | | 9/2018 | |
| WO | WO 2018/197897 A1 | | 11/2018 | |

OTHER PUBLICATIONS

Castro, J.L, et al., Enhancement of Oral Absorption in Selective 5-H 1d Receptor Agonists: Fluorinated 3-[3-(piperidin-1-yl)propyl] indoles, J. Med. Chem., vol. 41, No. 15, pp. 2667-2670 (Year: 1998).*
Limanto, J., et al., An efficient chemienzymatic approach fo (s)-gama-Fluoroleucine ethyl ester, J. Org. Chem., vol. 70, No. 6, pp. 2372-2375 (Year: 2005).*
Burmakov, A.I. et al., "Interaction of Oxy and Carbonyl Compounds With Sulfur," Journal of Organic Chemistry, Vol. XXII, No. 6 (1986).
Combined Search and Examination Report for corresponding Great Britain application GB1903909.8 dated Aug. 28, 2019, 12 pages.
Katagiri, Toshimasa et al., "A chemistry of 2,3-epoxy-1,1,1-trifluoropropane," Journal of Fluorine Chemistry, 105 (2000) 285-293.
Olah, George A. et al, "Synthetic Methods and Reactions.43. Preparation of Fluorohydrins from Epoxides with Pyridinium Polyhydrogen Fluoride," Israel Journal of Chemistry, vol. 17, No. 1-2, 1978, pp. 148-149.
Skupin, Rolf et al., "Regioselectivity of the ring opening of propene oxides bearing electron-withdrawing substituents at the methyl group with Olah's reagent," Journal of Fluorine Chemistry 92 (1998) 157-165.
Yoneda, Norihiko, "The Combination of Hydrogen Fluoride With Organic Bases as Fluorination Agents," Tetrahedron vol. 47, No. 29, pp. 5329-5365, 1991.
International Preliminary Report on Patentability for corresponding International application No. PCT/GB2020/050701, dated Sep. 16, 2021.
International Search Report for corresponding International application No. PCT/GB2020/050701, dated Oct. 16, 2020.
Written Opinion of the International Searching Authority for corresponding International application No. PCT/GB2020/050701, dated Oct. 16, 2020.
A.M. Semenopva, et al., "Transesterification of Dialkyl Carbonates with 2,2,3,3,-Tetrafluoropropan-1-ol," Russian Journal of Organic Chemistry, Maik Nauka—interperiodica, RU, vol. 55, No. 6, Sep. 7, 2019, pp. 771-774.
Christopher J. Cramer, et al., "Perfluorocarbenes Produced by Thermal Cracking. Barriers to Generation and Rearrangement," Journal of organic Chemistry, vol. 64, No. 13, Jan. 1, 1999, pp. 4850-4859.
Daiki Nishikawa, et al., "Thermal and oxidation stability of organi-fluorine compound-mixed electrolyte solutions for litium ion batteries," Journal of Power Sources, Elsevier SA, Ch, vol. 243, Jun. 15, 2013, pp. 573-580.
George A. Olah, et al., "Synthetic Methods and Reactions.43. Preparation of Fluorohydrins from Epoxides with Pyridinium Polyhydrogen Fluoride," Israel Journal of Chemistry, vol. 17, 1978, pp. 148-149.
Julia A. Kalow, et al., "Enantioselective Ring Opening of Epoxides by Fluoride Anion Promoted by a Cooperative Dual-Catalyst System," Journal of American Chemical Society, ol. 132, No. 10, 2010, pp. 3268-3269.
Martin R. Bryce, et al., "Reactions Involving Fluoride Ion. Part 30. Preparation and Reactions of Epoxides Derived from Perfluoroalkyl Substituted Alkenes," Journal of the Chemical Society, Perkin Transactions 1, Royal Society of Chemistry, Cambridge, UK, No. 7, Jan. 1, 1984, pp. 1391-1395.
P Brewer et al., "Synthesis and Some Novel Reactions of $\alpha,\alpha$ Dichloroperfluoroalkyl Esters," J. Org. Chem., 1961, 26 12, Dec. 1, 1961, pp. 5091-5099.
T.I. Gorbunova, et al., "Symmetrical Fluorinated Dialkyl Carbonates as Precursors of Promising Materials," Russian Journal of Applied Chemistry, Pleiades Publishing, Moscow, vol. 91, No. 4, Jun. 30, 2018, pp. 657-662.
Takashi Achiha, et al., "Electrochemical Behavior of Nonflammable Organo-Fluorine Compounds for Lithium Ion Batteries," Journal of the Electrochemical Society, vol. 156, No. 6, Jan. 1, 2009, pp. A483-A488.
Takashi Achiha, et al., "Thermal Stability and Electrochemical Properties of Fluorine Compounds as Nonflammable Solvents for Lithium-Ion Batteries," Journal of the Electrochemical Society, vol. 157, No. 6, Jan. 1, 2010, pp. A707-A712.
Toshimasa Katagiri, et al., "A chemistry of 2,3-epoxy-1,1,1-trifluoropropane," Journal of Fluroine Chemistry, Elsevier, NL, vol. 105, No. 2, Sep. 1, 2000, pp. 285-293.
Viacheslav A. Petrov, et al., "New partially fluorinated expoxides by oxidation of olefins with sodium hypoalites under phase transfer catalysis," Journal of Fluorine Chemistry, Elsevier, NL, vol. 125, No. 1, Jan. 1, 2004, pp. 99-105.
Yuki Matsuda, et al., "Safety improvement of lithium ion batteries by organo-fluorine compounds," Journal of Fluorine Chemistry, vol. 132, No. 12, Jul. 19, 2011, pp. 1174-1181.

* cited by examiner

METHOD FOR PREPARING PARTIALLY FLUORINATED ALCOHOL

CROSS-REFERENCE TO RELATED APPLICATIONS

This application is the U.S. National Stage application of PCT application no. PCT/GB2020/050701, filed on Mar. 18, 2020, titled COMPOSITION, designating the United States, which claims priority to Great Britain application no. 1903909.8, filed on Mar. 21, 2019, the contents of which are each incorporated herein by reference in their entirety.

The present invention relates to methods of preparing partially fluorinated alcohols (fluorohydrins) from fluorinated epoxides and preparing fluorinated carbonate esters from fluorohydrins.

Fluorohydrins are useful as solvents and as synthetic building blocks from which various species such as esters, ethers, ketones, aldehydes and acids can be prepared. Of particular interest is their utility in the preparation of fluorinated carbonate esters, which are an important class of materials with significant commercial value. Fluorinated carbonate esters are commonly used without modification as synthetic intermediates and as solvents in electronic devices such as batteries (e.g. lithium ion batteries) and to manufacture products such as lubricants, sealants, and coatings.

The production of fluorohydrins from epoxides is known in the art. For example, Olah described a general method for preparing fluorohydrins by ring opening epoxides with a nucleophilic source of fluoride (G. A. Olah et al, Israel Jr. Chem., 17(1978), 148-149). However, Olah did not extend this work to the preparation of fluorohydrins from fluorinated epoxides.

The ring opening of the fluorinated epoxide, 2,3-epoxy1, 1,1-trifluoropropane (TFPO), with various nucleophiles to form fluorohydrins was generally described in a review of the chemistry of TFPO by Uneyama in Jr. Fluorine Chem., 105(2000) 285-293. However, this review was silent on the possibility or likely outcome of attempting to ring open TFPO or indeed any other fluorinated epoxide with nucleophilic fluorinating agents as taught by Olah.

General methods for the production of carbonate esters from alcohols and a carboxylating agent are known in the art, see for example "March's Advanced Organic Chemistry", M. B. Smith and J. March, 6th edition, page 1276. However, the production of fluorinated carbonate esters from fluorohydrins and carboxylating agents is unknown as are the products of such reactions.

METHODS OF THE INVENTION

According to a first aspect of the invention there is provided a method for preparing a partially fluorinated alcohol, comprising reacting a fluorinated epoxide:

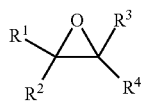

wherein $R^1$, $R^2$, $R^3$ and $R^4$ are independently selected from the group comprising H, F, Cl, Br, I, $CF_3$, alkyl, fluoroalkyl, haloalkyl with a fluorinating agent.

Preferably at least one of $R^1$ to $R^4$ comprises F, $CF_3$ or fluoroalkyl.

Preferably the fluorinating agent comprises a nucleophilic fluorinating agent. Preferred examples of fluorinating agents include HF and complexes of HF with nitrogen containing species, such as Olah's reagent (HF:Pyridine complex), with urea, or with a tertiary amine.

The method may comprise reacting an epoxide of 3,3,3-Trifluoropropene (1243zf) with HF and/or Olah's reagent to form $CF_3CH(OH)CH_2F$.

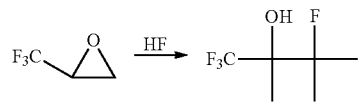

The method may comprise reacting an epoxide of 1,3,3,3-Tetrafluoropropene (1234ze) with HF and/or Olah's reagent to form $CF_3CH(OH)CHF_2$.

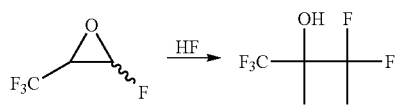

The method may comprise reacting an epoxide of 1,1,1,4,4,4-hexafluoro-2-butene (1336mzz) with HF and/or Olah's reagent to form $CF_3CH(OH)CHF(CF_3)$.

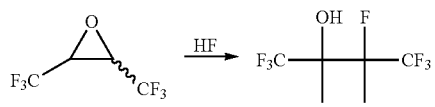

The method may comprise reacting an epoxide of 1,1,3,3,3-Pentafluoropropene (1225zc) with HF and/or Olah's reagent to form $CF_3CH(OH)CF_3$.

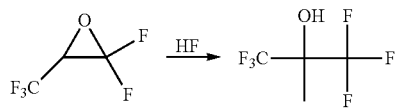

COMPOUNDS & COMPOSITIONS OF THE INVENTION

According to a second aspect of the invention there is provided compounds with the structure

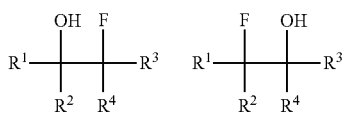

wherein $R^1$, $R^2$, $R^3$ and $R^4$ are independently selected from the group comprising H, F, Cl, Br, I, $CF_3$, alkyl, fluoroalkyl, haloalkyl, with the provision that the compound is not 1,1,1,3-tetrafluoropropan-2-ol.

The compounds of the second aspect of the invention may be used in the preparation of a carbonate ester.

According to a third aspect of the invention there is provided a method for preparing a partially fluorinated carbonate ester with the structure

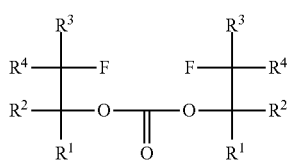

comprising reacting a fluorohydrin

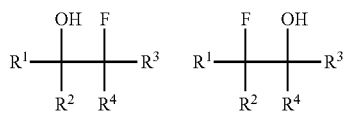

wherein $R^1$, $R^2$, $R^3$ and $R^4$ are independently selected from the group comprising H, F, Cl, Br, I, $CF_3$, alkyl, fluoroalkyl, haloalkyl with $COX_2$, wherein X is selected from the group comprising —F, —Cl, —$OCH_3$, —$OCCl_3$, imidazole, succinimidyl.

Preferably 2 equivalents (on a molar basis) of the fluorohydrin are used per 1 equivalent of $COX_2$.

Alternatively, 1 equivalent of the fluorohydrins of this invention maybe used with 1 equivalent of an alcohol species (a branched or linear monohydric/polyhydric alcohol) to prepare asymmetric carbonate esters.

The compounds produced in a method according to the third aspect of the invention are covered by the fourth aspect of the invention. According to the fourth aspect of the invention there is provided a compound with the structure

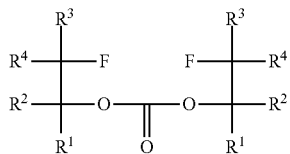

wherein $R^1$, $R^2$, $R^3$ and $R^4$ are independently selected from the group comprising H, F, Cl, Br, I, $CF_3$, alkyl, fluoroalkyl, haloalkyl.

The compounds of the fourth aspect of the invention may be also used as a battery solvent component (e.g. in a lithium ion battery). Here the compounds are found to be beneficial as a result of their physical properties, electrochemical stability, compatibility with battery components such as battery electrodes (cathodes and anodes) including electrodes comprising carbon and silicon, lithium containing electrolyte salts, separators, binders, current collectors and low flammability.

The compounds of the fourth aspect of the invention may also be used with other solvents and additives such as other linear and cyclic carbonate esters.

Preferably when used as a solvent the composition comprises an electrolyte salt. Preferred examples of electrolyte salts include lithium-based electrolytes such as those selected from the group comprising lithium hexafluorophosphate ($LiPF_6$), lithium triflate ($LiSO_3CF_3$), lithium bis(fluorosulfonyl)imide ($Li(FSO_2)_2N$) and lithium bis(trifluoromethanesulfonyl)imide ($Li(CF_3SO_2)_2N$).

The compounds of the second aspect of the invention may be used in the preparation of a (more highly) fluorinated derivative. One or more of the R groups may be substituted by fluorine. In the process the R groups to be altered by fluorination are preferably selected from the group comprising H, Cl, Br, I.

Depending on the nature of the R group(s) being modified the preparation process for the fluorinated derivative may comprise a multi-stage process; preferably a two-stage process. In a preferred two stage process a first stage is the modification of the targeted R group(s) to a (different) halogen group, preferably to a chlorine group (with a suitable chlorinating agent such as chlorine); in a second stage the chlorine group is modified to a fluorine group (with a suitable fluorinating agent such as HF or a metal fluorine salt, such as NaF, KF). It will be appreciated that where the R group(s) targeted already comprises a halogen, other than fluorine, a two-stage process with substitution of the halogen with chlorine may not be necessary.

Thus compounds

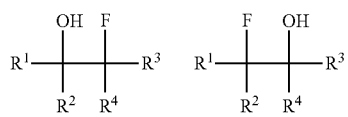

wherein at least 2 of $R^1$ to $R^4$ independently comprises H, Cl, Br, I may be converted to (more highly) fluorinated derivatives.

In the fluorinated derivatives preferably at least 2 and more preferably at least 3 of $R^1$ to $R^4$ independently comprises F, $CF_3$ or a fluoroalkyl. Preferably at least 1 of $R^1$ to $R^4$, and more preferably 1 of $R^1$ to $R^4$ independently comprises H. Most preferably 1 of $R^1$ to $R^4$ comprises $CF_3$, two of $R^1$ to $R^4$ comprise F and one of $R^1$ to $R^4$ comprises H. Most preferably the fluorinated derivative comprises hexfluoroisopropanol.

A preferred reaction pathway occurs for the compound

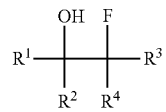

wherein in the preferred alternatives
$R^1$ is —$CF_3$, $R^2$ is H and both $R^3$ and $R^4$ are H.
$R^1$ is —$CF_3$, $R^2$ is H; one of $R^3$ and $R^4$ is H, one of $R^3$ and $R^4$ is F.

This preferred pathway is shown below.

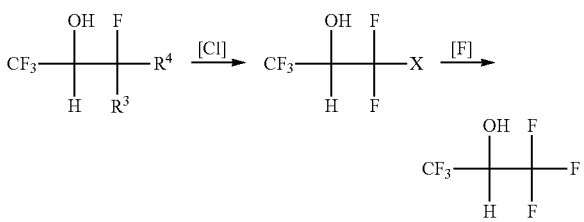

X is either F or Cl.

The epoxides useful in the first aspect of the invention may prepared from a fluorinated alkene. According to a fifth aspect of the invention there is provided a method for preparing a partially fluorinated epoxide, comprising reacting a fluorinated alkene:

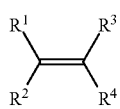

wherein $R^1$, $R^2$, $R^3$ and $R^4$ are independently selected from the group comprising H, F, Cl, Br, I, $CF_3$, alkyl, fluoroalkyl, haloalkyl with an oxidising agent.

Preferably at least one of $R^1$ to $R^4$ comprises F, $CF_3$ or fluoroalkyl.

Preferred examples of oxidising agent include air, oxygen and oxygen containing compounds such as peroxides, persalts and compounds of oxygen with other elements such as hypohalites. Preferably the oxidising agent comprises a hypohalite such as chlorite.

Preferably, the compound reacted with the oxidising agent is a tetrafluoropropene. Most preferably, one of $R^1$ and $R^2$ is —$CF_3$ and one of $R^3$ and $R^4$ is —F. Thus, the tetrafluoropropene is 1,3,3,3-Tetrafluoropropene (1234 ze) or 2,3,3,3-Tetrafluoropropene (1234yf).

According to a sixth aspect of the invention there is provided a method for preparing a fluorohydrin comprising the fifth and the first aspects of the invention.

According to a seventh aspect of the invention there is provided a method for preparing a partially fluorinated ether with the structure

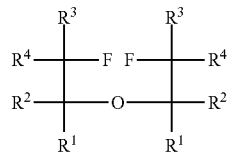

comprising reacting a fluorohydrin with the structure

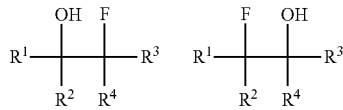

wherein $R^1$, $R^2$, $R^3$ and $R^4$ are independently selected from the group comprising H, F, Cl, Br, I, $CF_3$, alkyl, fluoroalkyl, haloalkyl.

According to an eighth aspect of the invention there is provided a compound with the structure

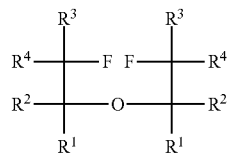

wherein $R^1$, $R^2$, $R^3$ and $R^4$ are independently selected from the group comprising H, F, Cl, Br, I, $CF_3$, alkyl, fluoroalkyl, haloalkyl.

According to a ninth aspect of the invention there is provided a composition comprising a compound of the eighth aspect of the invention.

The compound of the eighth aspect of the invention or the composition according to the ninth aspect of the invention may be used as a solvent, for example, in battery applications.

The compound of the eight aspect of the invention or the composition according to the ninth aspect of the invention may be used as a coolant, for example, as an immersive coolant.

Also provided is a method for preparing a partially fluorinated ether with the structure

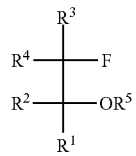

comprising reacting a fluorohydrin with the structure

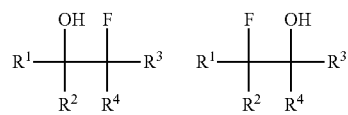

wherein $R^1$, $R^2$, $R^3$, $R^4$ are independently selected from the group comprising H, F, Cl, Br, I, $CF_3$, alkyl, fluoroalkyl, haloalkyl and $R^5$ is independently selected from the group $CF_3$, alkyl, fluoroalkyl, perfluoroalkyl, haloalkyl perfluorohaloalkyl.

Preferably the ether synthesis occurs via acid catalysed dehydration of the fluorohydrin.

Alternatively the ether synthesis occurs via one or more of the following techniques:

i. Alkoxy-de-halogenation—reaction of an alkyl halide with a fluorohydrin, preferably under basic conditions;
ii. Alkoxy-de-sulphonyloxy-substitution—reaction of an fluorohydrin sulphate with an alkoxide or fluorohydrin alkoxide;
iii. Hydro, alkoxy-de-diazo-disubstitution—reaction of a fluorohydrin with a diazo compound;
iv. Alkoxy-de-hydroxylation—dehydration of two alcohols to yield an ether with e.g. concentrated sulphuric acid;
v. Hydroxy or alkoxy-de-alkoxylation—transetherification of a (fluorohydrin)ether with an alcohol or fluorohydrin; and/or
vi. Alkoxy-de-hydroxylation—reaction of an alcohol or fluorohydrin with an oxonium compound.

Additionally provided is a compound with the structure

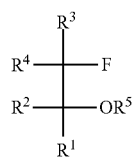

Further provided is a composition comprising a compound with the structure

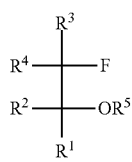

The compound or the composition may be used as a solvent, for example, in battery applications.

The compound or the composition may be used as a coolant, for example, as an immersive coolant.

The invention will now be illustrated with reference to the following non-limiting examples.

EXAMPLES

Example 1—Ring Opening of an Epoxide with Olah's Reagent

The following steps were followed.

The reactor was charged with Olah's reagent (70% HF:Pyridine, 5 ml) and cooled in an ice batch with stirring.

2,3-epoxy1,1,1-trifluoropropane (TFPO) (3.4 g) was then added dropwise.

At the end of the addition the reaction mixture was allowed to warm up to room temperature; stirring was continued for 48 hours.

After 48 hours the reaction mixture was quenched with ice.

Salt was added, and the product extracted with diethyl ether (3×5 ml). The diethyl ether extracts were combined, washed with saturated potassium bicarbonate solution and water before being dried over anhydrous sodium sulphate. Diethyl ether was removed in vacuo to yield the desired product as a clear, colourless liquid boiling point 91-93° C. The identity of this product was confirmed by NMR spectroscopy.

Example 2—Ring Opening of 2,3-epoxy-1,1,1,3-tetrafluoropropane with Olah's Reagent

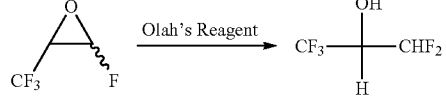

2,3-epoxy-1,1,1,3-tetrafluoropropane was ring opened using the following procedure:

A 100 ml Hastalloy C pressure reactor was charged with Olah's reagent (70% HF:Pyridine, 25 g).

After sealing, the contents of the reactor were cooled to 20° C. with stirring.

2,3-epoxy-1,1,1,3-tetrafluoropropane (11 g) was then added.

After this addition was complete the reaction mixture was heated to 50° C. and stirred for 168 hours.

After 168 hours the reaction mixture was quenched with ice and saturated sodium chloride solution (22 ml) added.

The product was extracted from this mixture with diethyl ether.

The diethyl ether extracts were combined, washed with saturated potassium bicarbonate solution and then water before being dried over anhydrous sodium sulphate. The identity of the product was confirmed by NMR spectroscopy.

Example 2a—Ring Opening of 2,3-epoxy-1,1,1,3-tetrafluoropropane with Olah's Reagent

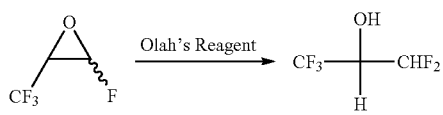 [SMILES: FC1OC1C(F)(F)F ; OC(C(F)F)C(F)(F)F]

2,3-epoxy-1,1,1,3-tetrafluoropropane was ring opened using the following procedure:

A 100 ml Hastalloy C pressure reactor was charged with Olah's reagent (70% HF:Pyridine, 25 g).

After sealing, the contents of the reactor were cooled to 20° C. with stirring.

2,3-epoxy-1,1,1,3-tetrafluoropropane (10.6 g) was then added.

After this addition was complete the reaction mixture was heated to 80° C. and stirred for 43 hours.

After 43 hours a sample of the reaction mixture was analysed by GCMS and it was found that all the feed epoxide had reacted.

After cooling the reaction mixture was quenched with ice and saturated sodium chloride solution (22 ml) added.

The product was extracted from this mixture with diethyl ether.

The diethyl ether extracts were combined, washed with saturated potassium bicarbonate solution and then water before being dried over anhydrous sodium sulphate. The identity of the product was confirmed by NMR spectroscopy.

Example 3—Ring Opening of 2,3-epoxy-1,1,1-trifluoro-2-(trifluoromethyl)propane with Olah's Reagent

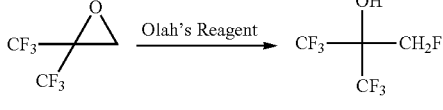

2,3-epoxy-1,1,1-trifluoro-2-(trifluoromethyl)propane was ring opened using the following procedure:

A 100 ml Hastalloy C pressure reactor was charged with Olah's reagent (70% HF:Pyridine, 16.5 g).

After sealing, the contents of the reactor were cooled to 20° C. with stirring.

2,3-epoxy-1,1,1-trifluoro-2-(trifluoromethyl)propane (10 g) was then added.

After this addition was complete the reaction mixture was heated to 50° C. and stirred for 160 hours.

After 160 hours the reaction mixture was quenched with ice and saturated sodium chloride solution (22 ml) added.

The product was extracted from this mixture with diethyl ether.

The diethyl ether extracts were combined, washed with saturated potassium bicarbonate solution and then water before being dried over anhydrous sodium sulphate. The identity of the product was confirmed by NMR spectroscopy.

Example 4—Preparation of di-(1,1,1,3-tetrafluoropropyl) carbonate with Phosgene

Di-(1,1,1,3-tetrafluoropropyl) carbonate was synthesised using the following procedure:
- A three necked round bottom flask was cooled to 0° C. under an inert atmosphere.
- Phosgene solution (15% by weight in toluene, 50 mL of solution) was added and stirred.
- A mixture of 1,1,1,3-tetrafluoropropan-2-ol (18.42 g) and pyridine (11.02 g) was added to the solution dropwise, and the temperature of the solution was monitored to ensure it did not rise above 10° C.
- The solution was allowed to warm to room temperature and stirred for 48 hours.
- The product was filtered to remove pyridinium salts and the solvent was removed in vacuo to yield the crude product.
- The crude product was distilled under atmospheric conditions to yield di-(1,1,1,3-tetrafluoropropyl) carbonate as a yellow oil (7.08 g, 35% yield).

FIGURES

The Figures illustrates the results of various spectroscopic analytical techniques carried out on some of the reaction products from the Examples.

Figure 1:
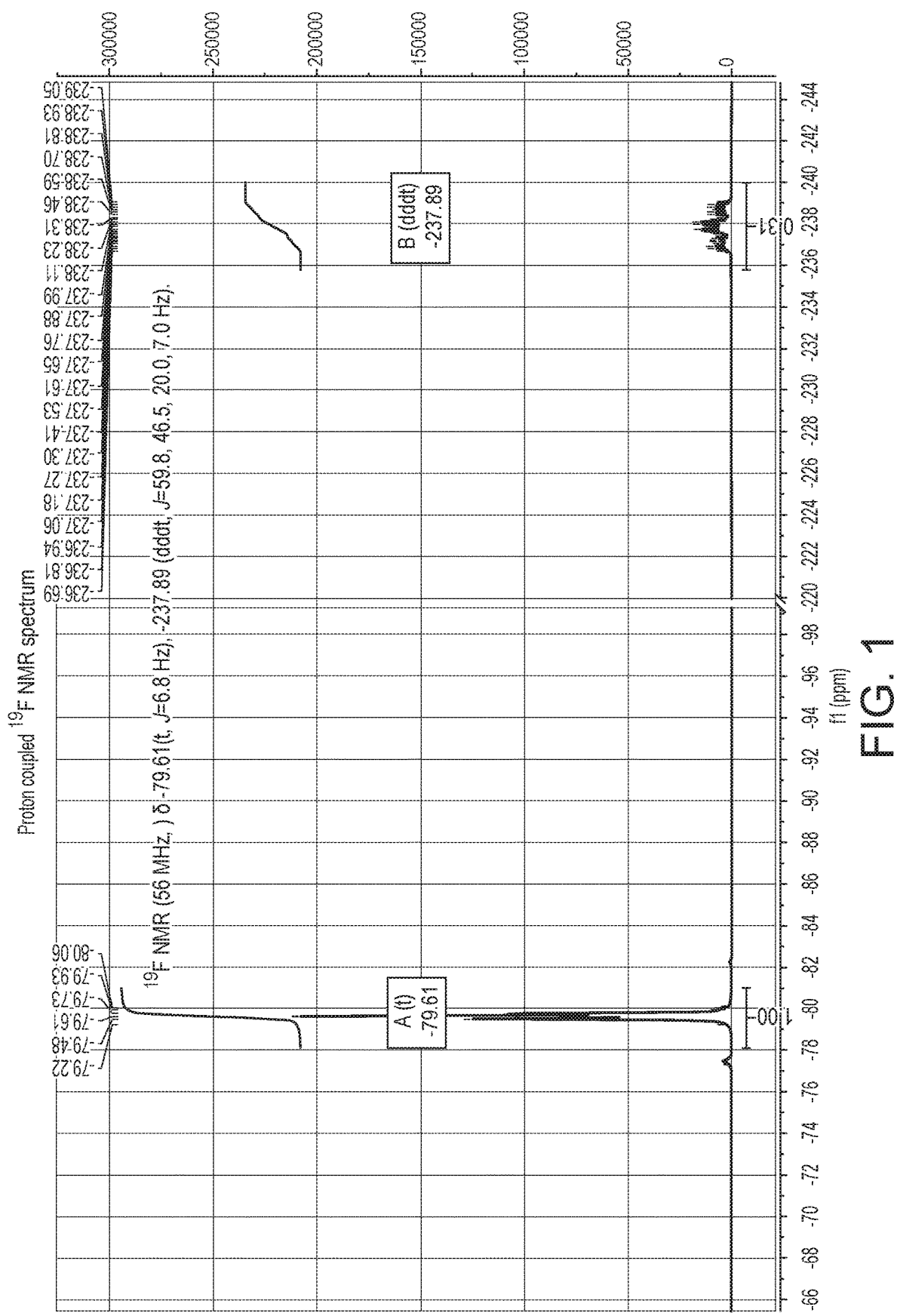
FIG. 1 shows a $^{19}$F NMR spectrum of the reaction product of 2,3-epoxy1,1,1-trifluoropropane (TFPO) with Olah's reagent.
Figure 2A:
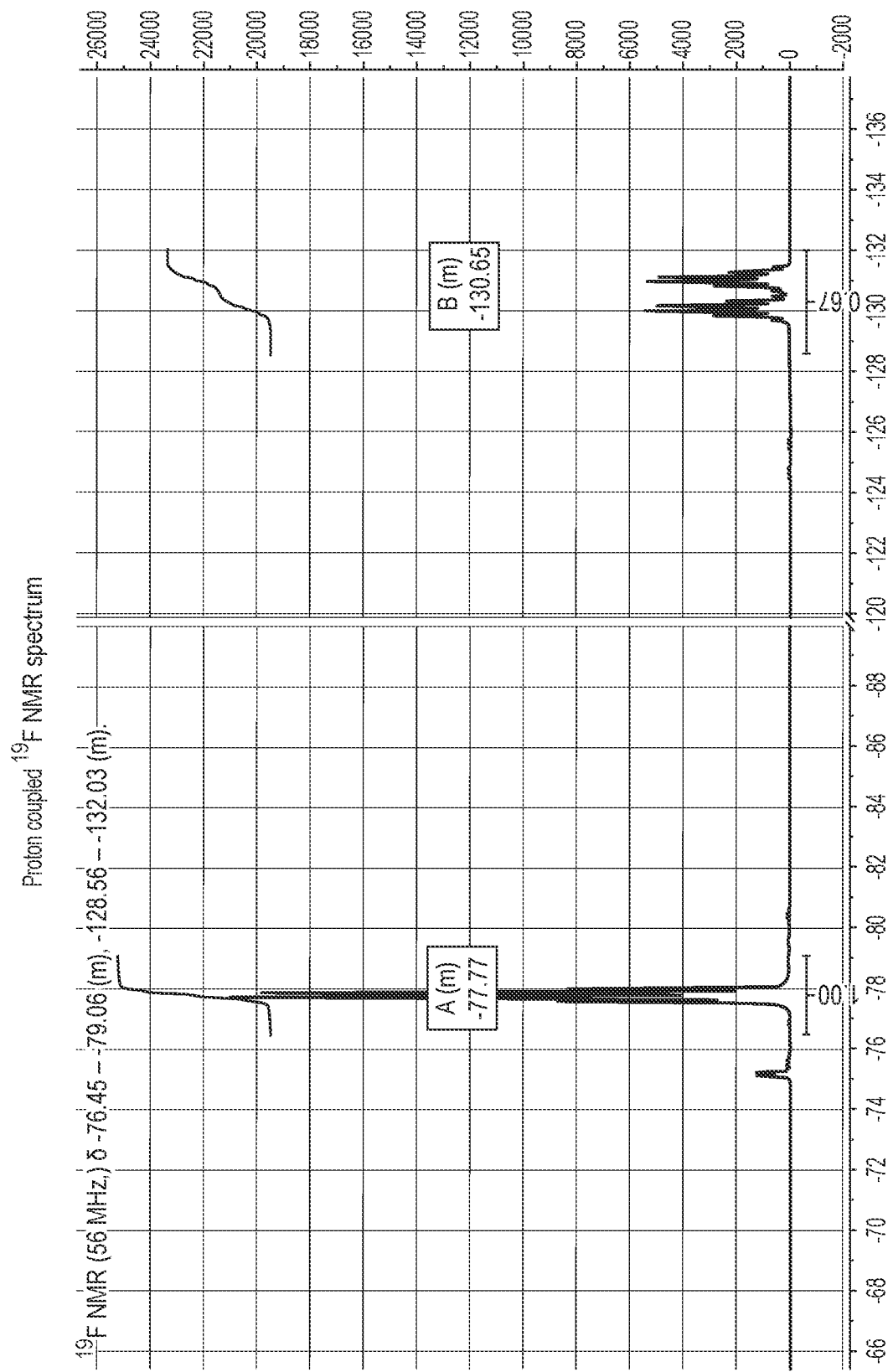
FIG. 2A shows a $^{19}$F NMR spectrum of the reaction product of 2,3-epoxy-1,1,1,3-tetrafluoropropane ring opening with Olah's reagent.
Figure 2B:
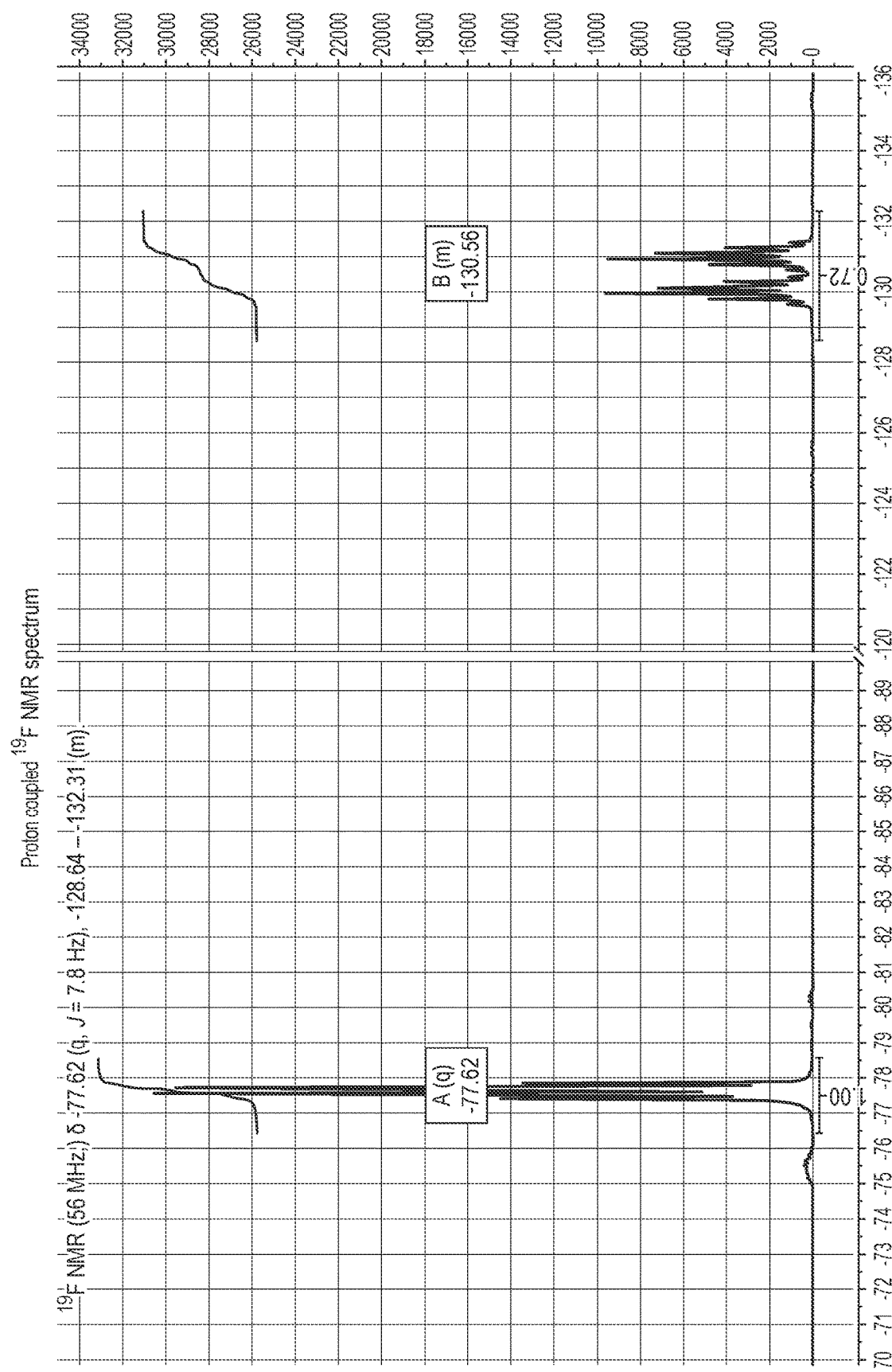
FIGS. 2B and 2C show a proton coupled and a proton decoupled $^{19}$F NMR spectrum of the reaction product of 2,3-epoxy-1,1,1,3-tetrafluoropropane ring opening with Olah's reagent.
Figure 2C:
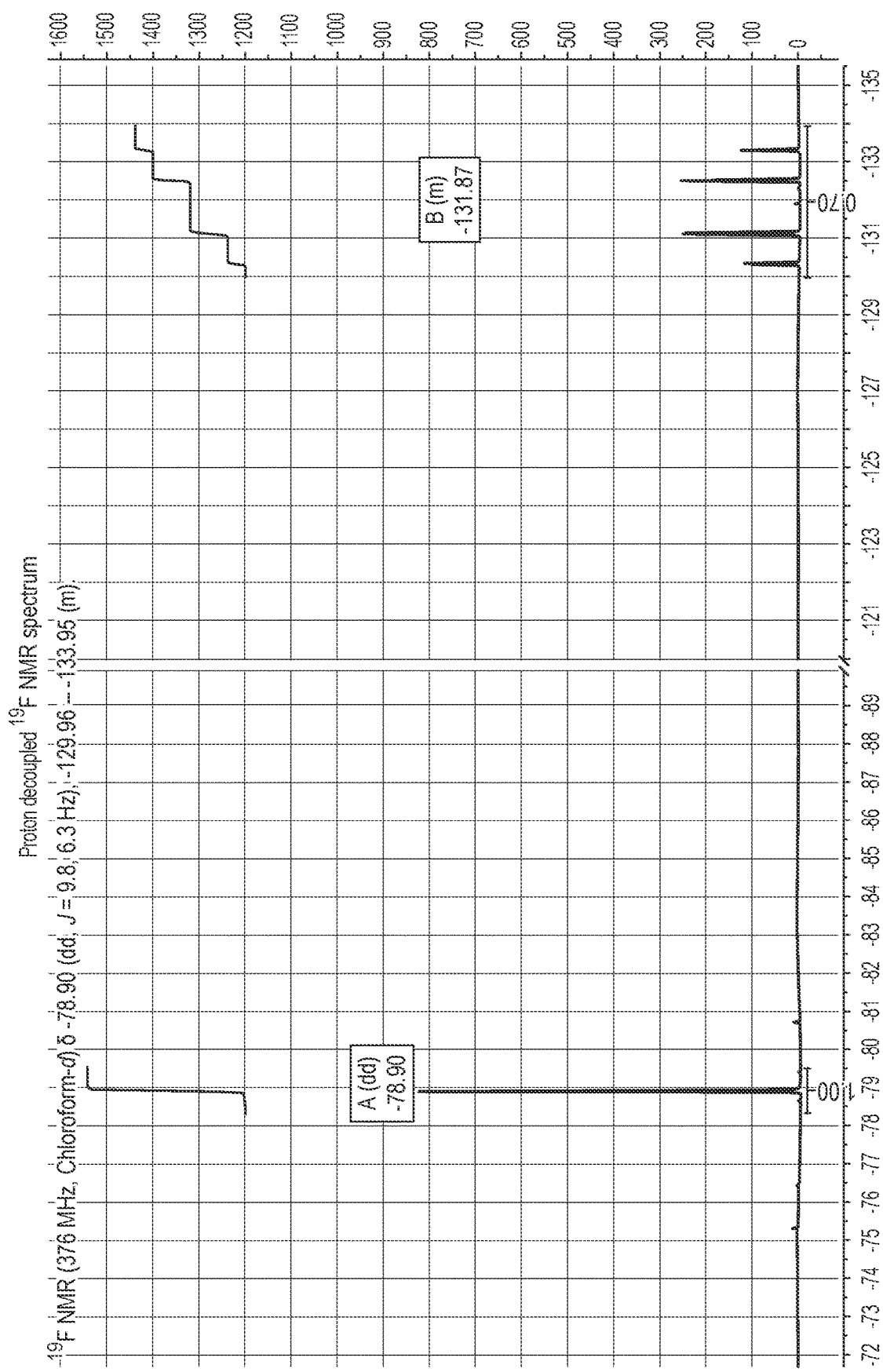
Figure 3:
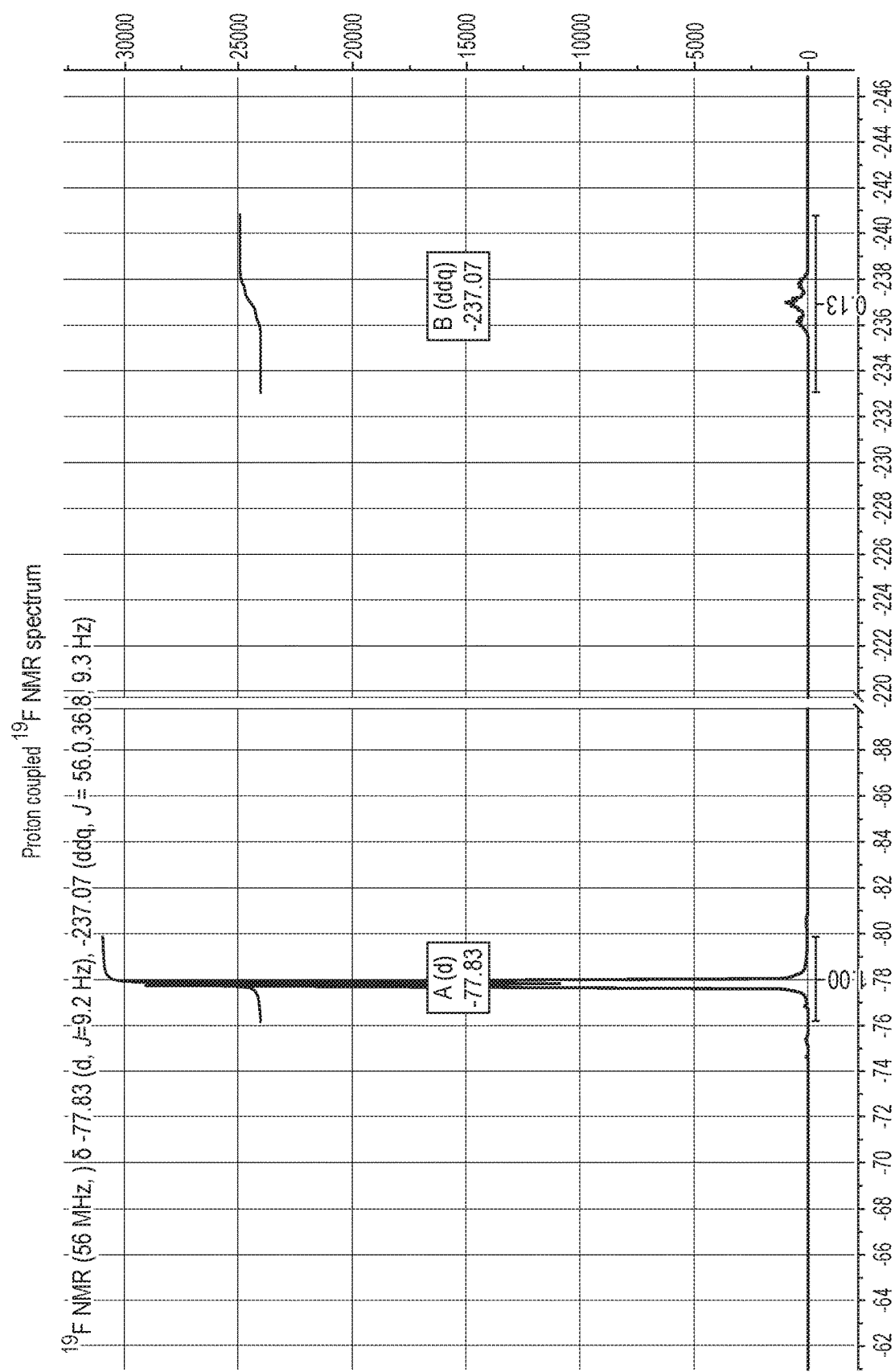
FIG. 3 shows a $^{19}$F NMR spectrum of the reaction product of 2,3-epoxy-1,1,1-trifluoro-2-(trifluoromethyl)propane) ring opening with Olah's reagent.
Figure 4:
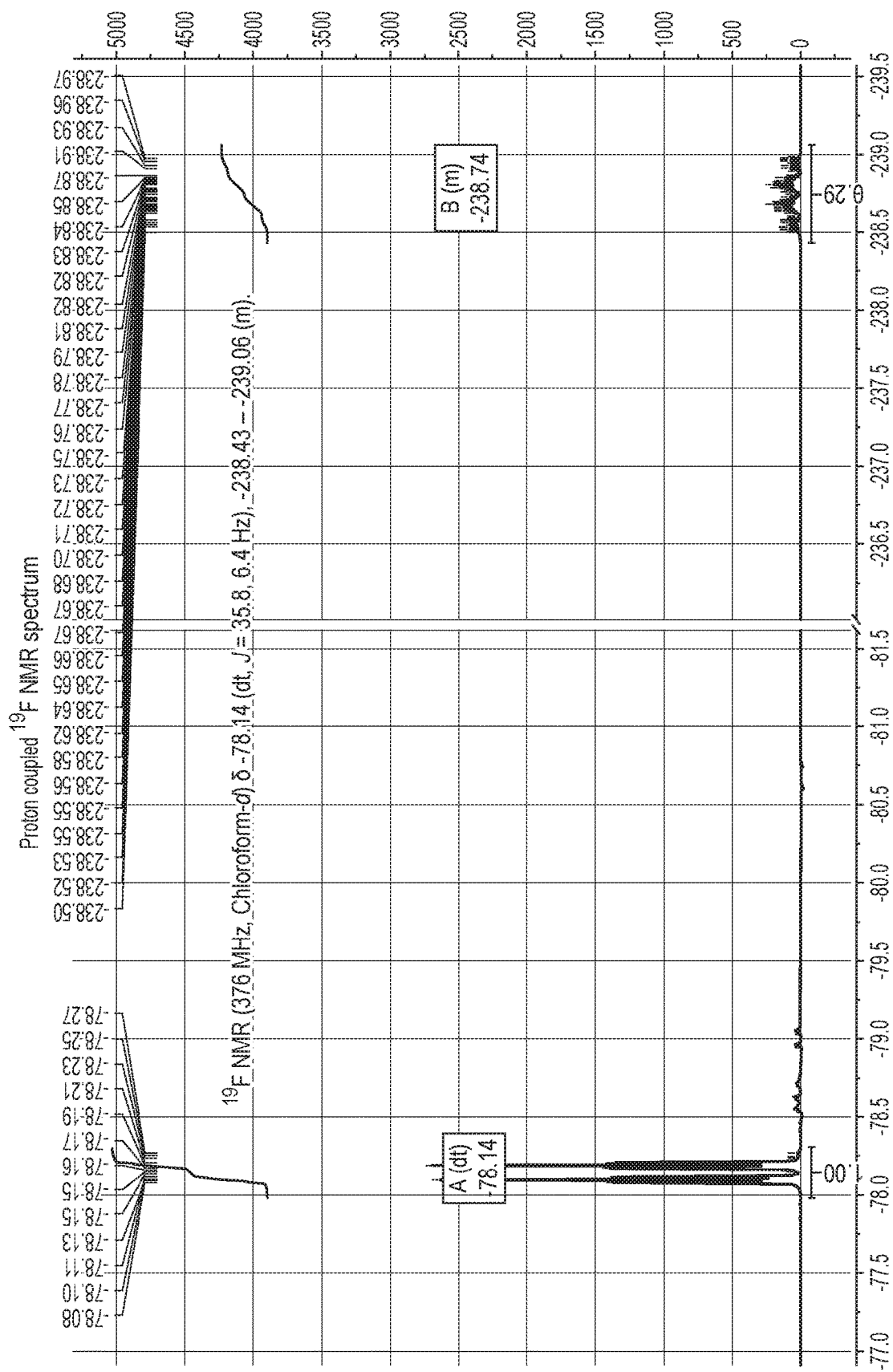
FIG. 4 shows a $^{19}$F NMR spectrum of the reaction product of 1,1,1,3-tetrafluoropropan-2-ol with phosgene, consistent with that of the product di-(1,1,1,3-tetrafluoropropyl) carbonate.

The invention claimed is:

1. A method for preparing a partially fluorinated alcohol, comprising:
reacting an epoxide:

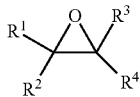

with a fluorinating agent;
wherein $R^1$, $R^2$, $R^3$ and $R^4$ are independently selected from the group consisting of H, F, Cl, Br, I, $CF_3$, alkyl, fluoroalkyl, and haloalkyl; where at least one of $R^1$, $R^2$, $R^3$ and $R^4$ is —$CF_3$, and at least one of $R^1$, $R^2$, $R^3$ and $R^4$ is —H.

2. The method according to claim 1, where the fluorinating agent comprises a nucleophilic fluorinating agent.

3. The method according to claim 1, where the fluorinating agent is selected from HF and complexes of HF with nitrogen containing species.

4. The method according to claim 3, where the complexes of HF with nitrogen containing species are selected from the group comprise Olah's reagent (HF:Pyridine complex), HF with urea, HF with a tertiary amine, or combinations thereof.

5. The method according to claim 1, where one of $R^1$ to $R^4$ is —$CF_3$, one of $R^1$ to $R^4$ is —F and two of $R^1$ to $R^4$ are —H.

6. The method according to claim 1, where two of $R^1$ to $R^4$ are —$CF_3$ and two of $R^1$ to $R^4$ are —H.

7. The method according to claim 1, where one of $R^1$ to $R^4$ is —$CF_3$ and three of $R^1$ to $R^4$ are —H.

8. The method according to claim 1, where one of $R^1$ to $R^4$ is —$CF_3$, one of $R^1$ to $R^4$ is —Cl and two of $R^1$ to $R^4$ are —H.

9. The method according to claim 4, where the complexes of HF with nitrogen containing species comprises Olah's reagent and the ratio of HF to pyridine is 7:3 by weight.

10. The method according to claim 5, where $R^1$ is —F and $R^3$ is —$CF_3$, $R^2$ and $R^4$ are —H; or $R^1$ is —F and $R^2$ is —$CF_3$, and $R^3$ and $R^4$ are —H.

11. The method according to claim 5, where or $R^1$ is —F and $R^2$ is —$CF_3$, and $R^3$ and $R^4$ are —H.

12. The method according to claim 6, where $R^1$ is —$CF_3$ and $R^3$ is —$CF_3$; $R^2$ is —H and $R^4$ is —H.

13. The method according to claim 7, where $R^1$ is —$CF_3$, $R^2$, and $R^3$ and $R^4$ are —H.

14. The method according to claim 8, where $R^1$ is —Cl, $R^3$ is —$CF_3$, and $R^2$ and $R^4$ are —H.

15. The method according to claim 8, where $R^1$ is —Cl, $R^2$ is —$CF_3$, and $R^3$ and $R^4$ are —H.

16. The method according to claim 1, with the provision that the partially fluorinated alcohol is not 1,1,1,3-tetrafluoropropan-2-ol.

17. The method according to claim 7, with the provision that the partially fluorinated alcohol is not 1,1,1,3-tetrafluoropropan-2-ol.

18. The method according to claim 1, further comprising preparing the epoxide by reacting a partially fluorinated alkene:

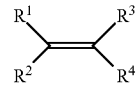

wherein $R^1$, $R^2$, $R^3$ and $R^4$ are independently selected from the group consisting of H, F, Cl, Br, I, $CF_3$, alkyl, fluoroalkyl, and haloalkyl, where at least one of $R^1$, $R^2$, $R^3$ and $R^4$ is —$CF_3$ and at least of one of $R^1$, $R^2$, $R^3$ and $R^4$ is —H;
with an oxidising agent to form a partially fluorinated epoxide.

19. The method according to claim 18, wherein the oxidising agent is selected from the group consisting of air, oxygen and oxygen containing compounds, where the oxygen containing compounds optionally comprise peroxides, per-salts or compounds of oxygen with other elements.

20. The method according to claim 18, wherein the oxidising agent comprises a hypohalite.

21. The method according to claim 18, wherein the alkene comprises a tetrafluoropropene or a pentafluoropropene.

22. The method according to claim 21, wherein the alkene comprises 1,3,3,3-tetrafluoropropene (1234ze) or 2,3,3,3-tetrafluoropropene (1234yf).

23. The method according to claim 21, wherein the alkene comprises 1,1,3,3,3-pentafluoropropene (1225zc).

24. The method according to claim 1, wherein the epoxide is a partially fluorinated epoxide, and the method further comprises reacting the partially fluorinated epoxide with a first fluorinating agent to form a compound having at least either of the following structures:

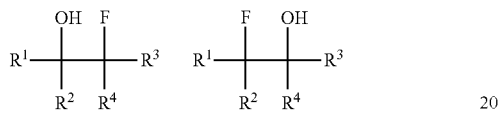

wherein at least two of $R^1$ to $R^4$ independently are H, Cl, Br, or I; and reacting the compound having the at least either of the above structures with a second fluorinating agent.

25. The method according to claim 20, wherein the oxidising agent comprises chlorite.

* * * * *